Figure 2:
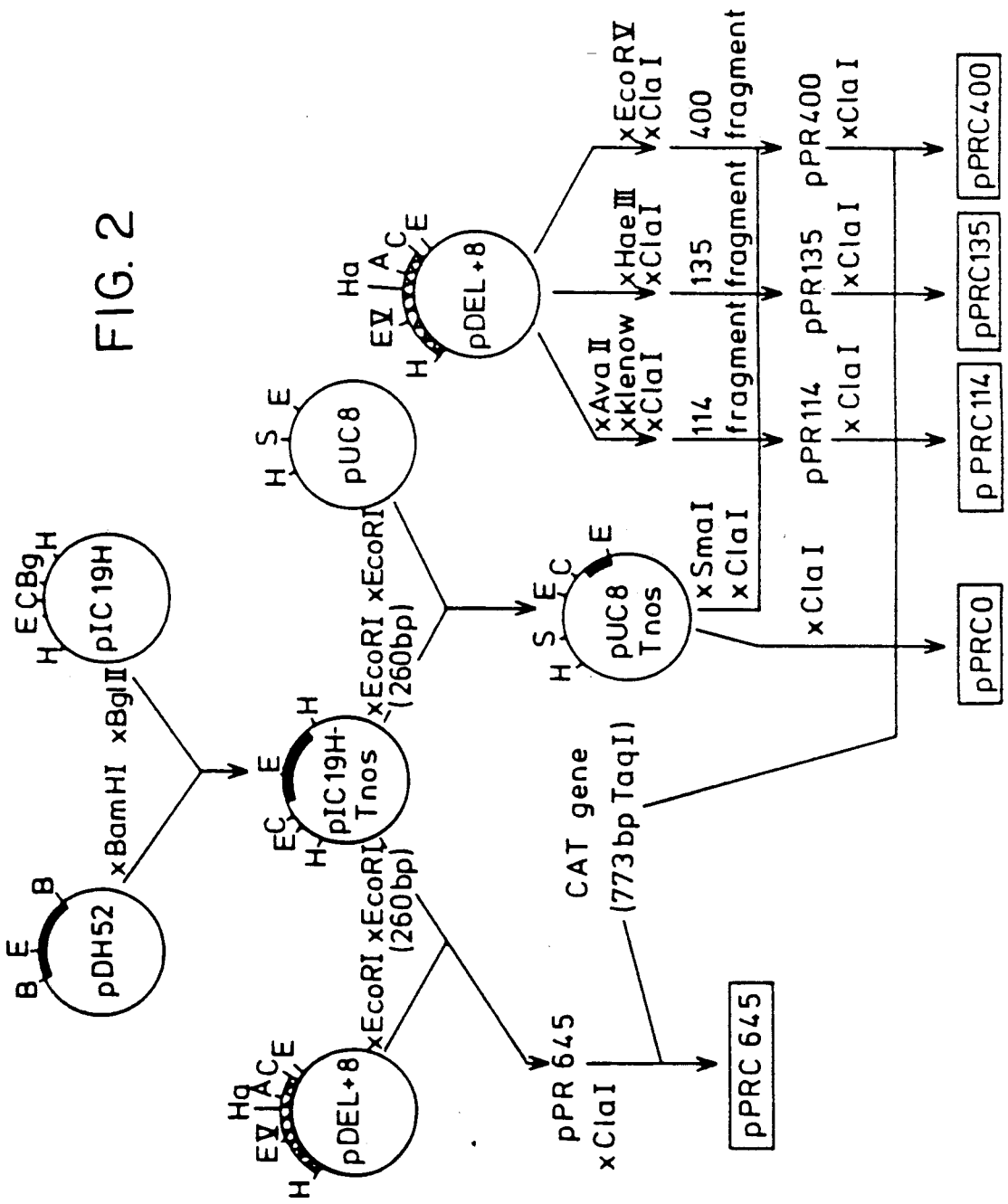

united States Patent [19]
Bol et al.

[11] Patent Number: 5,057,422
[45] Date of Patent: Oct. 15, 1991

[54] RECOMBINANT DNA: TRANSFORMED MICROORGANISMS, PLANT CELLS AND PLANTS: A PROCESS FOR INTRODUCING AN INDUCIBLE PROPERTY IN PLANTS, AND A PROCESS FOR PRODUCING A POLYPEPTIDE OR PROTEIN BY MEANS OF PLANTS OR PLANT CELLS

[75] Inventors: John F. Bol, Oegstgeest; Bernardus J. C. Cornelissen, Leiden; Johannes A. L. van Kan, Oegstgeest, all of Netherlands

[73] Assignees: Mogen International N.V.; Rijksuniversiteit Leiden, both of Leiden, Netherlands

[21] Appl. No.: 327,340

[22] Filed: Mar. 22, 1989

[30] Foreign Application Priority Data

Mar. 23, 1988 [NL] Netherlands ................ 8800725

[51] Int. Cl.⁵ ............... C12N 15/29; C12N 15/82; C12N 1/21; A01H 5/00
[52] U.S. Cl. .................. 435/240.4; 435/69.1; 435/70.1; 435/172.3; 435/252.3; 435/320.1; 536/27; 800/205; 935/35; 935/36; 935/64
[58] Field of Search ........... 435/320, 317.1, 172.3, 435/240.4, 252.3; 800/1–205; 536/27; 935/35, 36, 64

[56] References Cited

PUBLICATIONS

Thornburg et al., 1987 (Feb.), Proc. Natl. Acad. Sci., U.S.A., 84:744–748.
van Loon 1985, Pl. Molec. Biol., 4:111–116.
Hooft van Huijsduijnen et al. 1986, EMBO J. 5:2057–2061.
Condit et al., 1987 (Dec.), Molec. Cell Biol. 7:4273–4279.
Linthorst et al. 1989 (March), The Plant Cell 1:285–291.
Keller et al. 1988 (Dec.), EMBO J. 7:3625–3633.

Primary Examiner—Elizabeth C. Weimar
Assistant Examiner—P. Rhodes
Attorney, Agent, or Firm—Cooper & Dunham

[57] ABSTRACT

This invention relates to recombinant DNA comprising vector-DNA and a DNA sequence corresponding with, or relates to, a salicylate-inducible promoter of a GRP gene of plants, such as tobacco plants. The invention also relates to microorganisms, plant cells and plants transformed using the recombinant DNA, to a process for introducing an inducible property in plants and to a process for producing a polypeptide or protein, using plant cells and plants transformed using the recombinant DNA.

4 Claims, 5 Drawing Sheets

FIG. IA

```
TTTAAAAATTATATTATTGAATTGATATAAATATCGGATACGGACAGGAAATGAACAGCC
    -1780              -1760              -1740

TTTCAACTGATAAGGGACTGTTTGACATCTTGTGCTGCATTATCTTTTTCTTCATTCGTG
    -1720              -1700              -1680

TTTTAATTTGTAGGCCAGCAACCCCTTGCACGTGGTTTGACTCTTCCGATTCTCTCTCAA
    -1660              -1640              -1620

ATACTTGTTCTTAAATTAAAAATATGTATAAAATATCAAAAATACTTTTTATGACGTAAG
    -1600              -1580              -1560

CTATTTTCTACGTATCAATTTAGACGACGTAATTTGGTTTAACACAAAATTTATGAAAAA
    -1540              -1520              -1500

ATAAAGACCTTTAAATATATAGACTTAAAAGCTTTGTGGGATATTTGCGTACGTATAAAA
    -1480              -1460              -1440

GTTTTTCATTAAAATAAAGTGAGTAAAATGAAAAGTTTAAAGTTAAATTATTTTTAAATA
    -1420              -1400              -1380

TAAAAATATTTTATTCTGGAACGGATTAATAAAAATGTGTTATTTAATTACGAGAGTATG
    -1360              -1340              -1320

TCATATATATATATATATATATATATATATATATATATATATAGTCCTTAATAAGGAATCCA
    -1300              -1280              -1260

TTAGTAGATCAGGTTATTAATTTCTTTGTTTTTTTTTTTTTGGTTTTAAGCGACTACTT
    -1240              -1220              -1200

TATATTAGAATTAAAAATGTTTTGCAGGGAGTGGTTGCTCATAGGCAGCATTACAAAAGG
    -1180              -1160              -1140

TACTATGTAGAGCATAACCTACACTGGGATGCCTAGCTACACTAGTTGTACTGTTAGATG
    -1120              -1100              -1080

GAGGCGTAGCAATACTATTTAACATTGGTACATCAAAAATATTAATACTACTGCTACTAC
    -1060              -1040              -1020

AGACATTACTAGAAGATGGCTTATCCGAAGGTTGACAAAATTTGTTCATGTGTGTACGCC
    -1000              -980               -960

AGGCCTTTGCATTGAGATGTTTAGTTGCTGATCCTGGAGGAGATGTTTGAGGATGAAAGG
    -940               -920               -900

TGGAGGGTTGCTCAAAAAAGTGATGTTGCTCCATTCTTTGGAGTTAGACTGTGAAAATAT
    -880               -860               -840

TTTCTTTGTTTGACAATTAATCTTGACCTGGATTACTTGCTTTTTACTATAAAAAAATTA
    -820               -800               -780

AATTTAAATTTATGCTTTGAGAATAAGCGTAAGTTCAACTCTTTAAGAGAGGTGGAGCGA
    -760               -740               -720

GGATTTAAAATTTACGGGTTTGAGATTCTACTCCTTTTAAGTTATGAGAGATATTTTTAG
    -700               -680               -660
```

FIG. 1B

```
TAAGCTTTTTTATAAAATAAATATAGAATTTGAACAAAAACTACTACATTCAAACGCATCA
        -640              -620              -600
ATAACCTAAACTCTACTTCTCCTCTAGTTCAAGACTCTCTTCA[TGTGGAAA]TGACATTAG
        -580              -560              -540
                                                       64
GTAGCCATTTTAAACATGTTGTTTAAAATATATTCACAGTTTACAATGTATTTAAAGATT
        -520              -500          9   -480            9
AGCAATTTCGCTCAAACTTCAGGACATGGCGTCCTAGAGTTTAAACCTCAAAGTTTAAAC
        -460              -440              -420
TTCAAGATATCGTATCCTAAAGTTCGAAAATGTGTGTCCAGAAGTTTATGTCCTAAATT
     17  -400        18  -380           17  -360
TTAAATTAATAGTTAAAAAATTCATGACACTTAATCCTAAATTTCAAATTACCATCTCAA
        -340 18          -320              -300       64
AAATTCATGACACTTAGTCCAGAATTTTGGATGAATTAGCTCATCTTTTTACACATTATA
        -280              -260              -240
AATTGTAAATATATTTTAAATAGCGAGCTTAAAAGTGACTATTGCTGCACTTGGTCAGAC
        -220              -200              -180
TTCACGTTCACTCTCTTTACTGCCACTTGTAGGCCGGGTTTCTTCGTGTCTTTGGTCCAC
        -160              -140              -120
                                  CAAT
ACAATAATGTACATTTTCCCTCATACCTCCAAGTAGTACCATTCCCTTCAATTATTTATG
        -100              -80                       cap
                TATA                                 ↓
CATTCAAATCATACTATAAAGAGAACCCAAGAGTACATCAGTTTCTTCATCCCTTAATTT
        -40               -20                1
                                         M G S K A F L
CATAAGCATCATAACTAAACTTTGAACAAAAAAAGAAAACATGGGTTCTAAGGCATTTCT
        20                40                60
 F L G L C L A F F F L I S S E Y V A G E
GTTTCTTGGCCTTTGTTTGGCTTTTTTTTCCTGATAAGCTCTGAGGTTGTAGCTGGGGA
        80                100               120
 L A E T S N P→ Intron
ATTGGCTGAGACTTCCAACCGTAAGCTTACTCTCATTTTACTATGAAAAAATGAAAATCT
        140               160               180
CTTCTCTCATTATTTGATATAGGATTCAACTAATAATTATTTTGTATGCATTGAGTATTT
        200               220               240
TAACTGTTGTAACATTCTTTAACCTTTCAAATTAGTGTTTATCAGCTAGCAAAGCTCAAT
        260               280               300
TTAGTTTCCACATCGAGCTAGTAGTTGAGTTACATTACTATCGCTATAGCTTGATAATAA
        320               340               360
```

FIG. IC

```
CTCTTAATATGTAGTCCTTTTATTTCATTTTAAGTGTTTTAATTTGGATGGATATGAAGT
      380                 400                 420

TTAAATGAGAATGTAAGTAAAATCTTTGAATCTTGTGATTTTATAAAGTTGTATAAAAAC
      440                 460                 480

ATACCAAAAAATATCCTTTAAATCTTGTGGTCTTAAACATGTCTTGTATAAGAAGAGCCA
      500                 520                 540

TAAAGGGTAAAAATGAGAATGGTGGAACTTAAAACCTACTTATTGATTAAATATAGAAAG
      560                 580                 600

AGTATTTTTCTTAAAAAATAATAAAAGGAAAGAACGATACATAAATTGAAACATATGAAG
      620                 640                 660

M  K  L  D  G  E  N  G
TACTATGTATGTTTTAATTTTCATAATTGGTGCAGCAATGAAATTGGATGGCGAGAATGG
      680                 700                 720

V  D  V  D  G  R  G  G  Y  N  D  V  G  G  D  G  Y  Y  G  G
AGTAGACGTTGACGGACGTGGAGGATACAATGACGTTGGCGGCGATGGATATTATGGTGG
      740                 760                 780

G  R  G  R  G  G  G  G  Y  K  R  R  G  C  R  Y  G  C  C  R
TGGTCGCGGCCGTGGTGGTGGTGGTTATAAACGTAGAGGATGCCGCTATGGTTGCTGCAG
      800                 820                 840

K  G  Y  N  G  C  K  R  C  C  S  Y  A  G  E  A  M  D  K  V
GAAAGGTTACAATGGTTGCAAAAGGTGTTGTTCCTACGCAGGTGAGGCCATGGATAAAGT
      860                 880                 900

T  E  A  Q  P  H  N  *
CACTGAAGCTCAGCCTCACAACTGATCATTATGTGTAATATATAAAGAGTTTAAGTTATA
      920                 940                 960

TATGTCGTTAGTATATGTAACTTATACGTTGTGACAAGATGTAATAATCTTGCTACTTTA
      980                1000                1020

GACCTTGCTTGTAACAAGTATGAATAAAGCCATTCGGTTCTTATGGATGGTTGGTCATGT
      1040               1060        end of cDNA AATGTTTTGTTGTACAATATTTTGTGACAATATGTTTCCATATTGTTTATTTTCTTCATA
      1100               1120                1140

TTTTAGAGTAAAGGGTTTTCTTTTATTTTATGAATCCGACAATTTTCTTTTAATTTCATC
      1160               1180                1200

CGCGAATTTACAATTCAAGAAGAGATGGAGATCCAATACAACTAACGGGTTCTGGTTGAA
      1220               1240                1260

TTC
```

FIG. 3

1  2   3  4  5  6  7  8  9  10 11 12 13

— 1,3ac-cm

— 3ac-cm

— 1ac-cm

— cm

| W | S | — | W | S | W | S | W | S | W | S | W | S |
|---|---|---|---|---|---|---|---|---|---|---|---|---|
| 135 | | 645 | | 400 | | 135 | | 114 | | 35S | | |

RECOMBINANT DNA: TRANSFORMED MICROORGANISMS, PLANT CELLS AND PLANTS: A PROCESS FOR INTRODUCING AN INDUCIBLE PROPERTY IN PLANTS, AND A PROCESS FOR PRODUCING A POLYPEPTIDE OR PROTEIN BY MEANS OF PLANTS OR PLANT CELLS

A. Field of the Invention

This invention is in the field of DNA recombinant technology and is based on the identification of GRP (glycine-rich protein) genes occurring in plants with a salicylate-inducible promoter. More particularly the invention relates to the use of such a salicylate-inducible promoter.

B. State of the Art

Plants are continuously subject to influences from their environment, which may involve a threat. These influences may relate to such factors as temperature, light, humidity, salt and injuries, but also attack by pathogens, such as viruses, fungi, bacteria, insects and the like. For its survival, the plant has available a broad range of defensive mechanisms which are activated when the plant is subject to the "stress" conditions referred to. This activation is generally accompanied by the induction of the expression of specific plant genes. This induction is controlled by control elements often present in the promoter region upstream of the gene in question. A given stress factor may either activate a highly specific set of plant genes, or result in a broad response of many defense genes. Thus an increase in temperature for a short period of time leads to the expression of so-called "heat shock" (HS) protein genes; the plant is subsequently resistant to temperatures to which untreated plants are not resistant. A conserved sequence of about 14 basepairs occurring several times in the promoter region of HS protein genes has been found to be responsible for the induction of these genes (see e.g. Pelham and Bienz, 1982; Bienz, 1985).

Various light-inducible genes have meanwhile been cloned. When a sequence of several hundreds of basepairs located upstream of these genes is fused with a "reporter" gene, for example, the chloramphenicol-acetyl-transferase gene (CAT gene), this gene becomes light-inducible in transgenic plants (see e.g. Kuhlemeier et al., 1987; Green et al., 1987; Stockhous et al., 1987). In the promoter regions of a number of light-inducible genes, a common element of 9 basepairs can be distinguished, which is possibly involved in the light inducibility (Grob and Stuber, 1987).

When plants are injured, either mechanically or from being eaten by insects, plant genes are activated, inter alia, which code for proteinase inhibitors. These proteins, which are best characterized in tomato and potato, have virtually no effect on proteolytic enzymes of the plant but specifically inhibit digestive enzymes of animals, in particular those of insects. When a proteinase inhibitor gene of potato is induced by injury, it is found that, inter alia, base sequences are involved which are located downstream of the gene (Thornburg et al., 1987). When a proteinase inhibitor gene is placed under the control of a constitutive promoter (the CaMV-35S-promoter) and expressed in transgenic plants, the plant is found to have become highly resistant to insect damage (Hilder et al., 1987).

To be able to defend itself against infection by pathogens, the plant has a mechanism known by the name of "hypersensitive response". When, as a result of infection, this mechanism becomes activated, the plant cells infected die, and a lignin wall is formed around the centre of infection, which the pathogen is unable to pass. This means that infection results in necrotic lesions at the centres of infection, but the other parts of the plant remain virtually free of pathogen. Pathogens not activating the hypersensitive response may spread throughout the entire plant and become accumulated to high concentrations.

It has been found that in the case of a necrotic infection the pathogen-free parts of the plant develop a resistance to a second infection by a broad range of pathogens, such as viruses, fungi and bacteria ("acquired resistance"), no matter what type of pathogen caused the first infection. Thus a necrotic virus infection leads to resistance to fungi and vice versa. Owing to the necrotic infection, a large number of genes are induced in the pathogen-free parts of the plant (for a survey, see: Van Loon, 1982; Van Loon, 1985; Collinge and Slusarenko, 1987; Bol and Van Kan, 1988; Bol, 1988; Van Loon, 1988). It is supposed that products coded for by the induced genes play a role in the acquired resistance. Part of the induced genes code for enzymes which, starting from the amino acid phenylalanine, synthesize a diversity of aromatic compounds. These include compounds inhibiting the growth of fungi and called phytoalexins. They also include precursors of the lignin used in reinforcing cell walls and forming a barrier around a centre of infection. Another part of the induced genes codes for hydroxyproline-rich glycoproteins (HRGP, extensin) which are incorporated in the cell wall and function as a matrix for attaching aromatic compounds, such as lignin. A third group of induced genes, finally, codes for proteins which accumulate in the vacuole in the plant cell or are excreted in the intercellular space of the leaf. These so-called PR proteins (patho-genesis-related proteins) are best characterized in tobacco but occur in the plant kingdom in a highly conserved form. For one part they turn out to be hydrolytic enzymes, such as chitinases and glucanases, which in combination efficiently inhibit the growth of fungi on artificial media . Another PR protein is thought to inhibit the digestive enzymes of insects. The function of the other PR proteins is unknown.

White (1979) has found that the treatment of tobacco with certain aromatic compounds, such as salicylic acid (in the neutralized form) leads to the induction of a subgroup of PR proteins, i.e. the PR-1 proteins, and to a resistance to virus infection. This was seen as an indication that this subgroup of PR proteins is involved in the induced resistance to virus infection. Fraser (1983) argued against this that there are conditions which induce PR-1 proteins but do not generate an antiviral response. Hooft van Huijsduijnen et al. (1986) cloned DNA copies of six classes of messenger-RNA (mRNAs) which in Samsun NN tobacco are induced by tobacco mosaic virus (TMV) infection. Two of these classes of mRNAs are also induced by salicylate. One of these turned out to correspond to the PR-1 proteins. The other does not correspond to known PR proteins and was initially called "cluster C". Meanwhile the name has been changed into GRP-mRNA by reason of the discovery that it codes for a glycine-rich protein. This last suggests that the protein could be a cell wall component, comparable in function to the HGRP (Varner and Cassab, 1986). The copy DNAs (cDNAs) of the PR-1 mRNAa have been used as a probe for isolating clones of PR-1 genes with a genomic library of tobacco; the base sequence of these has been clarified (Cornelissen et al., 1987).

C. Description of the Invention

By hybridizing GRP-cDNA with a Southern blot of DNA of Nicotiana tabacum cv Samsun NN, it was found that the genome of tobacco contains about eight GRP genes. From a genomic library of Nicotiana tabacum cv. Samsun NN, four GRP genes were cloned. The base sequence of two of the cloned GRP genes was clarified. They were found to consist both of two exons coding for a protein of 109 amino acids. After splitting off a putative signal peptide, the mature protein consists as to about 25% of glycine and as to about 30% of charged amino acids. By S1-nuclease mapping, it was found that one of the two genes analysed is expressed. The sequence of this gene (clone gGRP-8) and the flanking DNA regions is given in FIG. 1. The other gene is probably not expressed in response to virus infection. From this, and from an analysis of the base sequence of cloned GRP-cDNAs, it can be concluded that at least three of the eight GRP genes are expressed after virus infection. The data obtained indicate that there is more than 80% homology between the coding sequences of the various GRP genes and also between the upstream DNA regions.

Fragments of the promoter region of the GRP gene in clone gGRP-8 were fused with the CAT-reporter gene. By means of the *Agrobacterium tumefaciens* technology, these constructs were integrated into the genome of tobacco, and the transgenic plants were tested for inducibility of the CAT gene by salicylate. In a reproducible manner, it was found that the first 114 nucleotides upstream of the transcription initiation site contain one or more elements which cause the promoter to become inducible by salicylate. This promoter was found to be also induced by several other substances, including acrylic acid, ethylene, and ethephone. Between the nucleotides −400 and −645 of FIG. 1, there are one or more elements which greatly enhance the salicylate-inducible activity of the promoter. If, therefore, a DNA fragment carrying the sequence of nucleotide −645 to +8 is coupled to any given gene, then, after transformation of plants with this construct, it will be possible for the gene in question to be induced with salicylate and several other specific aromatics in a controlled manner. At this moment, no other plant promoters have been characterized which can be regulated with a chemical effector in such a simple manner.

D. Further elaboration of the invention

The invention provides broadly recombinant DNA comprising vector-DNA and a DNA sequence corresponding to, or related to, a salicylate-inducible promoter of a GRP gene of plants.

The vector-DNA portion of the recombinant DNA according to the invention is not critical per se, and is determined by the contemplated use of the recombinant DNA, in particular the host to be transformed. Those skilled in the art know what vectors are suitable for given hosts. Known vectors which can be used in the *Agrobacterium tumefaciens* technology for the transformation of plants and plant cells are, for example, pAGS127 (van den Elzen et al, 1985) en pROK1(Baulcombe et al, 1986). Known vectors which can be used for cloning in bacteria, such as *Escherichia coli* are, for example, the various pUC plasmids.

As well known to those skilled in the art, the vector DNA will commonly, in addition to an origin of replication that is suitable to the host, also contain one or more marker genes, e.g., certain anti-biotic-resistant genes, in order that transformed hosts may be selected with facility.

The novel and inventive element in the recombinant DNA according to this invention consists in the DNA sequence which corresponds with or is related to, a salicylate-inducible promoter of a GRP gene of plants. FIG. 1 illustrates one concrete example of such a GRP gene, comprising a structural GRP gene and flanking regulation sequences. In nature, however, variants occur which are comprised by the present invention as far as they contain a salicylate-inducible promoter. The same applies to artificially constructed variants not demonstrated to be naturally occurring: these too are comprised by the present invention, provided they contain a salicylate inducible promoter. Of the flanking DNA sequences, only certain portions are responsible for the promoter function, the inducibility of the promoter by salicylate, and the strength of either the promoter or its inducibility by salicylate. Particularly in the other portions of the flanking regions, considerable variations are permissible. As regards the nucleotide sequence of the possible structural gene placed under the control of the promoter sequence, changes which do not affect the eventual sequence of amino acids will often be permissible. Changes leading to minor deviations in the sequence of amino acids will in many cases be still without consequences for the expression and function of the protein. The place, length and nucleotide sequence of introns can generally be varied as well, provided they can be processed by the host.

It should be noted that the term "GRP gene", as used herein, means not only the DNA coding for GRP, but, in a broader sense, the DNA involved in the expression of GRP, including the DNA coding for GRP (designated herein as structural GRP gene) and flanking DNA regions with regulating functions, including the GRP promoter.

Preferred embodiments of the invention described herein consist in the use of the GRP promoter for the following purposes.

1. Controlled production of commercially interesting proteins in plants

For the production through recombinant DNA techniques of proteins that have to undergo a post-translational modification, e.g., glycosylation, it is recommendable to use eukaryotic organisms. It is to be expected that, for this production, in addition to yeast and animal cells, plants can be used in future. By means of the GRP promoter, the production of the desired protein can be switched on at a controlled point of time by spraying or watering the plants with a solution containing millimolar quantities of sodium salicylate. This is in particular of importance when the protein to be produced is toxic to the plant or, for example, owing to a one-sided amino acid composition, forms a burden for the plant's metabolism. The salicylate can also be supplied through the ground water, when a local effect only is considered undesirable. In addition, in that case a separate step for rinsing off the salicylate, which when dried may induce necrosis on the leaves, can be done without. When the GRP promoter or derivatives thereof are fused with the code for a suitable signal peptide, there is the possibility of causing the desired protein to be secreted by the plant in the intercellular space of the leaf, from which it can be isolated in a simple manner in relatively pure form.

2. Controlled expression of genes in plants

Another possibility is the expression of genes to be controlled from the outside, with the object of controlling certain processes in the plant which, for example, are of interest for agricultural use. Thus genes involved in disease resistance could be expressed in a controlled manner. Also, this promoter, in combination with suitable genes involved in disease resistance, will react both rapidly and with great effectiveness in response to infection by a large group of pathogens, resulting in a more effective resistance reaction. This is the case, because the original GRP gene, for example after infection of tobacco with TMV, is one of the fastest and most efficiently reacting genes. The genes in question, controlled by the GRP promoter, may originate from the plant itself, or have been introduced from the outside and originate either from other plants or from other organisms (after being rendered suitable for expression and functioning of the gene product in the plant).

3. The controlled production of commercially interesting proteins in plant cell cultures Various biotechnologically oriented firms and institutions are at present investigating the possibility of utilizing large-scale cultures of genetically engineered plant cells for the production of proteins or secondary metabolites. In principle, there is the possibility of bringing the expression of an economically interesting gene under the control of the GRP promoter or derivatives thereof. Through standard techniques, cell cultures or root cultures can be obtained from plant material transformed by the *Agrobacterium tumefaciens* technology with the promoter/gene fusion construct in question. In such cell cultures, the gene concerned can be induced at the desired moment by adding sodium salicylate to the culture medium in millimolar quantities.

E. Examples

I. Cloning of GRP-cDNA

Polyadenylated RNA was isolated from tobacco mosaic virus infected tobacco and enriched through gradient centrifugation in molecules of 650 nucleotides (Hoofd van Huijsduijnen et al., 1986). Using standard techniques, well known to researchers in this field, the RNA could be copied by means of an oligo (dT) primer, reverse transcriptase and desoxyribonucleotide triphosphates in minus-strand DNA. Subsequently, using RNase H and DNA polymerase, a complementary DNA chain was synthesized on this DNA by the method of Gubler and Hoffman (1983). The double-stranded DNA was provided with C tails, which were hybridized with G tails, formed on the plasmid pUC9 after this had been cleaved with PstI (Maniatis et al., 1982). This construct was used for the transformation of E. coli MH-1. The transformants were striped in duplicate on nitrocellulose filters. One filter was hybridized with cDNA of poly(A)-RNA from TMV-infected tobacco, transcribed in vitro, the other filter was hybridized with cDNA against poly(A)-RNA from healthy tobacco (Maniatis et al., 1982). Transformants hybridizing better with the first probe than with the second contained cDNA of mRNAs induced by TMV infection. From these transformants, plasmid was isolated, the insert was subcloned in M13 vectors and the sequence of the insert was determined by the method of Sanger et al. (1977). Clones with sequences homologous to the sequence of nucleotides given in FIG. 1 contain the GRP-cDNA. As an alternative to the differential hybridization method, the cDNA library can be searched with a probe consisting of a desoxyoligonucleotide synthesized on the ground of the sequence of the GRP exons given in FIG. 1.

II. Cloning of GRP genes

DNA isolated from the nuclei of Samsun NN tobacco was partially digested with Sau3A I and cloned in the vector Charon 35 (for references, see: Cornelissen et al., 1987). The genomic library was searched with the plaque hybridization technique of Benton and Davis (1977), using the cDNA isolated in Example I as a probe. The insert in positively hybridizing phages contained the GRP gene and could be subcloned in pUC9 plasmids in parts through standard techniques.

III. Determination of GRP promoter activity

The construction of GRP promoter/CAT gene fusions is illustrated diagrammatically in FIG. 2. A HindIII fragment of gGRP-8 containing the sequence of nucleotides −645 to +155 was subcloned. From position +155, deletions were made with Ba131, whereafter the ends were provided with ClaI linkers by standard techniques. HindIII-ClaI fragments were subcloned in the vector pUCC and characterized by means of sequence analysis. One deletion mutant (pDEL+8) turned out to contain the sequence of from −645 to +8 and accordingly lacks the ATG initiation codon of the GRP gene.

The polyadenylation signal of the nopaline-synthase gene (Tnos) was isolated from plasmid pDH52 (Van Dun et al., 1987) as a 2 kb BamHI fragment and cloned in pIC19H (Marsh et al., 1984), which yielded pIC19H-Tnos. From this plasmid, Tnos can be cut as a 260 bp EcoRI fragment and subcloned in pUC8, which produced pUC8-Tnos. This 260 bp Tnos fragment was also subcloned in pDEL+8 downstream of the GRP promoter. Finally, the CAT gene of transposon Tn9 (Alton and Vapnek, 1979) was isolated as a 773 bp TaqI fragment from the pCaMV-CAT plasmid (Fromm et al., 1985) and cloned in the ClaI site of construct pPR645, which produced plasmid pPRC645.

Fragments of pDEL+8 were subcloned in pUC8-Tnos as blunt ClaI fragments. Subsequently, the 733 bp TaqI fragment was integrated in these constructs with the CAT gene. The promoter fragments of pDEL+8 fused with the CAT gene by this route were cut at the 3' site with ClaI at position +8 and at the 5', site with the enzymes EcoRV (at position −400), HaeIII at position −135) or AvaII (at position −114), respectively. The corresponding plasmids were called pPRC400, pPRC135 and pPRC114. These three plasmids and the pPRC645 plasmid were linearized with HindIII and cloned in the HindIII site of the binary transformation vector pAGS127. The CaMVCAT plasmid was cloned as an XbaI fragment in pAGS127. The resulting constructs were transferred to *Agrobacterium tumefaciens*, strain LBA4404 (Ooms et al., 1982), and the transconjugants were used to transform Samsun NN with the leaf disc method by standard procedures. Transgenic plants regenerated from shootlets, were tested by punching discs from the leaf and causing these to float on water or a solution of 1 mM salicylic acid for 24 h. Protein extracts of these discs were tested for CAT activity according to Gorman et al (1982). FIG. 3 shows the results. In lanes 1 and 2,400 μl protein was used, in the other lanes 100 μl. In lanes W and S, protein was used from discs floated respectively on water and salicylic acid. In lane 3, protein was used which had been isolated immediately after punching leaf discs. Lanes 6 up to and including 11 show that GRP promoter sequences of 400, 135 and 114 bp give the same degree of salicylic acid inducible CAT activity. Although relatively low, this activity is significant, as can be seen after magnifying the signal in lanes 1 and 2. The construct with the 645 bp promoter region gives a much higher activity. The CAT activity in the leaf discs floated on water (lane 4) has probably been induced through wounding the leaf during punching. Here again, the CAT activity is considerably stimulated by salicylic acid. The conclusion can be drawn that elements responsible for the salicylic acid inducibility are present in the region between nucleotides −114 and +8, while one or more enhancer elements are present between nucleotides −645 and −400.

F. Description of the Drawings

FIG. 1 shows the sequence of nucleotides of the structural GRP gene and the flanking DNA regions in gGRP-8 clone. The GRP reading frame has been aligned with the corresponding sequence of amino acids. The bold vertical arrow after the first 26 amino acids indicates the putative splitting site of a signal peptide. Initiation and termination signals involved in the transcription and translation procedures are underlined. The place of direct repeats with lengths of 17 and 18 basepairs and of inverted repeats with lengths of 9 and 64 basepairs are indicated by horizontal arrows. Putative activator elements are boxed or indicated by a waveline.

FIG. 2 diagrammatically shows the construction of GRP-promoter/CAT gene fusions. In it, use has been made of the known pDH52 plasmid which contains the polyadenylation signal of the nopaline-synthase gene (Tnos), of the known pIC19H and pUC8 plasmids, of the known pCaMV-CAT plasmid which contains the CAT gene of transposon Tn9, and of a plasmid pDEL+8, the construction of which is described herein.

FIG. 3 shows the results of tests in which the CAT activity was assayed in protein extracts of leaf discs of transgenic plants. The CAT activity was determined by the method of Gorman et al (1982). For further description, see the text.

G. Literature

Alton, N.K. and Vapnek, D. (1979) Nature 282, 864–869.

Baulcombe, D.C., Saunders, G.R., Bevan, M.W., Mayo, M.A., and Harrison, B.D. (1986) Nature 321, 447–449.

Bienz, M. (1985) TIBS 10, 157–161.

Bol, J.F. (1988) In: Plant Gene Research: temporal and spatial regulation of plant genes (D.P.S. Verma and R. Goldberg, eds.), Springer-Verlag, at pers. Bol, J.F. and Van Kan, J.A.L. (1988) Microbiological Sciences 5, 47–52.

Collinge, D.B. and Slusarenko, A.J. (1987) Plant Mol. Biol. 9, 389–410.

Cornelissen, B.J.C., Horowitz, J., Van Kan, J.A.L., Goldberg, R.B. and Bol, J.F. (1987) Nucleic Acids Res. 15, 6799–6811.

Fraser, R.S. and Clay, C.M. (1983) Neth. J. of Plant Pathol. 89, 283–292.

Fromm, M., Taylor, L.P. and Walbot, V. (1985) Proc. Natl. Acad. Sci. USA 82, 5824–5828.

Gorman, C.M., Moffat, L.F. and Howard, B.H. (1982) Mol. Cell. Biol. 2, 1044–1051.

Green, P.J., Kay, S.A. and Chua, N.—H. (1987) EMBO J. 6, 2543–2549.

Grob, U. and Stuber, K. (1987) Nucleic Acids Res. 15, 9957–9973.

Gubler, U. and Hoffman, B.J. (1983) Gene 25, 263–269.

Hilder, V.A., Gatehouse, A.M.R., Sheerman, S.E., Barker, R.F. and Boulter, D. (1987) Nature 300, 160–163.

Hooft van Huijsduijnen, R.A.M., Van Loon, L.C., Bol, J.F. (1986) EMBO J. 5, 2057–2061.

Kuhlemeier, C., Green, P.J. and Chua, N.H. (1987) Annu. Rev. Plant Physiol. 38, 221–257.

Maniatis, T., Fritsch, E.F. and Sambrook, J. (1982) Molecular Cloning, Cold Spring Harbour Lab. Marsh, J.L., Erfle, M and Wykes, E.J. (1984) Gene 32, 481–485.

Ooms, G., Hooykaas, P.J.J., Van Veen, R.J.M., Van Beelen, P., Regensburg-Tuink, A.J.G. and Schilperoort, R.A. (1982) Plasmid 7, 15–29.

Pelham, H.R.B. and Bienz, M. (1982) EMBO J. 1, 1473–1477.

Sanger, F., Nicklen, S. and Coulson, A.R. (1977) Proc. Natl. Acad. Sci. USA 74, 5463–5467.

Stockhous, J., Eckes, P., Rocha-Sosa, M., Schell, J. and Willmitzer, L. (1987) Proc. Natl. Acad. Sci. USA 84, 7943–7947.

Thornburg, R.W., An, G., Cleveland, T.E., Johnson, R. and Ryan, C.A. (1987) Proc. Natl. Acad. Sci. USA 84, 744–748.

Van den Elzen, P.J.M., Lee, K.Y., Townsend, J. and Bedbrook, J (1985) Plant Mol. Biol. 5, 149–154.

Van Dun, C.M.P., Bol, J.F. and Van Vloten Doting, L. (1987) Virology 159, 299–305.

Van Loon, L.C. (1982) In: Active defense mechanisms in plants (Wood, R.K.S. ed.), Plenum Press, New York, 247–273.

Van Loon, L.C. (1985) Plant Mol. Biol. 4, 111–116.

Van Loon, L.C. (1988) In: Plant-microbe interactions; molecular and genetic perspectives (Nester, E.W. and Kosuge, T., eds.) Macmillan Publ. Co., at pers. Varner, J.E. and Cassab, G.I. (1986) Nature 323, 110.

White, R.F. (1979) Virology 99, 410–412.

We claim:

1. Recombinant DNA comprising vector-DNA and a DNA sequence of nucleotide −645 to +8 of the GRP gene in clone gGRP8, or a variant or portion thereof, having a salicylate inducible promoter activity.

2. Recombinant DNA as claimed in claim 1, comprising vector-DNA and a salicylate-inducible promoter of a GRP gene of Nicotina tabacum cv. Samsun NN.

3. Recombinant DNA as claim in claim 1, further comprising a structural gene different from the structural GRP gene under the control of the GRP promoter.

4. Microorganisms, plant cells and plants transformed using recombinant DNA as claimed in claim 8, and progeny thereof which still contain the promoter sequence introduced.

* * * * *